(12) United States Patent
Furneaux et al.

(10) Patent No.: US 7,109,331 B2
(45) Date of Patent: Sep. 19, 2006

(54) 5H-PYRROLO[3,2-D]PYRIMIDINE NUCLEOSIDE METABOLISM INHIBITORS

(75) Inventors: Richard Hubert Furneaux, Wellington (NZ); Peter Charles Tyler, Wellington (NZ); Vern L. Schramm, New Rochelle, NY (US)

(73) Assignees: Industrial Research Limited, Auckland (NZ); Albert Einstein College of Medicine of Yeshiva University, Bronx, NY (US)

(*) Notice: Subject to any disclaimer, the term of this patent is extended or adjusted under 35 U.S.C. 154(b) by 0 days.

(21) Appl. No.: 10/363,424

(22) PCT Filed: Aug. 24, 2001

(86) PCT No.: PCT/NZ01/00174

§ 371 (c)(1),
(2), (4) Date: Oct. 3, 2003

(87) PCT Pub. No.: WO02/18371

PCT Pub. Date: Mar. 7, 2002

(65) Prior Publication Data

US 2004/0053944 A1    Mar. 18, 2004

(30) Foreign Application Priority Data

Aug. 29, 2000  (NZ) ........................ 506613

(51) Int. Cl.
C07D 487/04  (2006.01)
(52) U.S. Cl. .................................... 544/280
(58) Field of Classification Search ............. 514/265.1; 544/280
See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,228,847 B1 | 5/2001 | Furneaux et al. | |
| 6,379,911 B1 | 4/2002 | Schramm et al. | |
| 6,458,799 B1* | 10/2002 | Montgomery et al. | 514/265.1 |
| 6,492,347 B1 | 12/2002 | Furneaux et al. | |
| 6,660,719 B1* | 12/2003 | Bantia et al. | 514/43 |
| 6,693,193 B1 | 2/2004 | Furneaux et al. | |
| 6,764,829 B1 | 7/2004 | Schramm et al. | |
| 6,803,455 B1 | 10/2004 | Furneaux et al. | |
| 2004/0110772 A1 | 6/2004 | Furneaux et al. | |
| 2004/0181063 A1 | 9/2004 | Furneaux et al. | |

FOREIGN PATENT DOCUMENTS

WO  WO 99/19338   4/1999
WO  WO 00/61783   10/2000

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Bzowska A, Kulikowska E, Shugar D., Pharmacol Ther. Dec. 2000;88(3):349-425.*
Pugmire MJ, Ealick SE, Biochem J. Jan. 1, 2002,361(Pt 1):1-25.*
Anonymous, BioCryst News. Apr. 29, 1998.*

* cited by examiner

Primary Examiner—Thomas C. McKenzie
(74) Attorney, Agent, or Firm—Amster, Rothstein & Ebenstein LLP

(57) ABSTRACT

The present invention provides a compound of the formula (I):

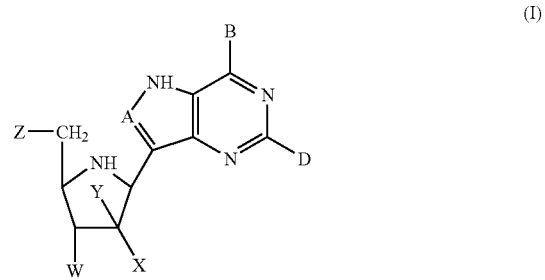

wherein A is selected from N, CH and CR, where R is selected from halogen, optionally substituted alkyl, aralkyl and aryl, OH, $NH_2$, $NHR^1$, $NR^1R^2$ and $SR^3$, where $R^1$, $R^2$ and $R^3$ are each optionally substituted alkyl, aralkyl or aryl groups; B is selected from OH, $NH_2$, $NHR^4$, H and halogen, where $R^4$ is an optionally substituted alkyl, aralkyl or aryl group; D is selected from OH, $NH_2$, $NHR^5$, H, halogen and $SCH_3$, where $R^5$ is an optionally substituted alkyl, aralkyl or aryl group; X and Y are independendy selected from H, OH and halogen, with the proviso that when one of X and Y is hydroxy or halogen, the other is hydrogen; Z is OH, or, when X is hydroxy, Z is selected from hydrogen, halogen, hydroxy, SQ and OQ, where Q is an optionally substituted alkyl, aralkyl or aryl group; and W is OH or H, with the proviso that when W is OH, then A is CR where R is as defined above; or a tautomer thereof; or a pharmaceutically acceptable salt thereof; or an ester thereof. The invention also provides pharmaceutical compositions comprising compounds of formula (I), methods of preparing compounds of formula (I), and methods of treatment using compounds of formula (I).

18 Claims, No Drawings

5H-PYRROLO[3,2-D]PYRIMIDINE NUCLEOSIDE METABOLISM INHIBITORS

STATEMENT OF GOVERNMENT SUPPORT

The invention disclosed herein was made with U.S. Government support under grant number GM41916 from the National Institutes of Health, U.S. Department of Health and Human Services. Accordingly, the U.S. Government has certain rights in this invention.

This is a U.S. national phase of PCT Application No. PCT/NZ01/00174, filed Aug. 24, 2001, and claims priority to NZ Application No. 506613, filed Aug. 29, 2000.

TECHNICAL FIELD

This invention relates to certain nucleoside analogues, pharmaceutical compositions containing the compounds and processes for preparing the compounds.

BACKGROUND OF THE INVENTION

Purine nucleoside phosphorylase (PNP) catalyses the phosphorolytic cleavage of ribo- and deoxytribonucleosides, for example, those of guenine and hypoxanthine to give the corresponding sugar-1-phosphate and guanine, hypoxanthine, or other purine bases.

Humans deficient in purine nucleoside phosphorylase (PNP) suffer a specific T-cell immunodeficiency due to an accumulation of dGTP and its toxicity to stimulated T lymphocytes. Because of this, inhibitors against PNP are immunosuppressive, and are active against T-cell malignancies. Clinical trials are now in progress using 9-(3-pyridylmethyl)-9-deazaguanine in topical form against psoriasis and in oral form for T-cell lymphoma and immunosuppression (BioCryst Pharmaceuticals, Inc). The compound has an $IC_{50}$ of 35 nM for the enzyme. In animal studies, a 50 mg/kg oral dose is required for activity in a contact sensitivity ear swelling assay in mice. For human doses, this would mean approximately 3.5 grams for a 70 kg human. With this inhibitor, PNP is difficult to inhibit due to the relatively high activity of the enzyme in blood and mammalian tissues.

Nucleoside and deoxynucleoside hydrolyses catalyse the hydrolysis of nucleosides and deoxynucleosides. These enzymes are not found in mammals but are required for nucleoside salvage in some protozoan parasites. Purine phosphoribosyltransferases (PPRT) catalyze the transfer of purine bases to 5-phospho-α-D-ribose-1-pyrophosphate to form purine nucleotide 5'-phosphates. Protozoan and other parasites contain PPRT which are involved in essential purine salvage pathways. Malignant tissues also contain PPRT. Some protozoan parasites contain purine nucleoside phosphorylases which also function in purine salvage pathways. Inhibitors of nucleoside hydrolases, purine nucleoside phosphorylases and PPRT can be expected to interfere with the metabolism of parasites and therefore be usefully employed against protozoan parasites. Inhibitors of PNP and PPRT can be expected to interfere with purine metabolism in malignant tissues and therefore be usefully employed against malignant tissues.

The applicants' PCT International Patent publication WO 99/19338 describes compounds which are potent inhibitors of PNP, PPRT and/or nucleoside hydrolases.

It is an object of the present invention to provide further compounds which are effective inhibitors of PNP, PPRT and/or nucleoside hydrolases, or at least to provide the public with a useful choice.

SUMMARY OF THE INVENTION

Accordingly, in a first aspect, the present invention provides a compound of the formula:

(I)

wherein:

A is selected from N, CH and CR, where R is selected from halogen, optionally substituted alkyl, aralkyl and aryl, OH, $NH_2$, $NHR^1$, $NR^1R^2$ and $SR^3$, where $R^1$, $R^2$ and $R^3$ are each optionally substituted alkyl, aralkyl or aryl groups;

B is selected from OH, $NH_2$, $NHR^4$, H and halogen, where $R^4$ is an optionally substituted alkyl, aralkyl or aryl group;

D is selected from OH, $NH_2$, $NHR^5$, H, halogen and $SCH_3$, where $R^5$ is an optionally substituted alkyl, aralkyl or aryl group;

X and Y are independently selected from H, OH and halogen, with the proviso that when one of X and Y is hydroxy or halogen, the other is hydrogen;

Z is OH, or, when X is hydroxy, Z is selected from hydrogen, halogen, hydroxy, SQ and OQ, where Q is an optionally substituted alkyl, aralkyl or aryl group; and W is OH or H, with the proviso that when W is OH, then A is CR where R is as defined above;

or a tautomer thereof; or a pharmaceutically acceptable salt thereof; or an ester thereof; or a prodrug thereof.

Preferably when B is $NHR^4$ and/or D is $NHR^5$, then $R^4$ and/or $R^5$ are $C^1$–$C^4$ alkyl.

Preferably when one or more halogens are present they are chosen from chlorine and fluorine.

Preferably when Z is SQ or OQ, Q is $C_1$–$C_5$ alkyl or phenyl.

Preferably D is H, or when D is other than H, B is OH.

More preferably, B is OH, D is H, OH or $NH_2$, X is OH or H, Y is H, most preferably with Z as OH, H, or methylthio, especially OH.

In certain preferred embodiments W is OH, Y is H, X is OH, and A is CR where R is methyl or halogen, preferably fluorine.

In other preferred embodiments, W is H, Y is H, X is OH and A is CH.

It will be appreciated that the representation of a compound of formula (I) wherein B and/or D is a hydroxy group used herein is of the enol-type tautomeric form of a corresponding amide, and this will largely exist in the amide form. The use of the enol-type tautomeric representation is simply to allow fewer structural formulae to represent the compounds of the invention.

According to another aspect of the invention, there is provided a pharmaceutical composition comprising a pharmaceutically effective amount of a compound of the formula (I) as defined above.

In another aspect, the invention provides methods for treatment of diseases or conditions in which it is desirable to decrease the level of T lymphocyte activity, the method comprising administering to a mammal in need of such treatment a pharmaceutically effective amount of a compound as defined above.

In a further aspect, the invention provides methods for treatment and/or prophylaxis of parasitic infections, particularly those caused by protozoan parasites, the method comprising administering to a mammal in need of such treatment a pharmaceutically effective amount of a compound as defined above.

In further aspects, the invention provides methods of preparing compounds of formula (I) as defined above.

While the invention is broadly as defined above, it is not limited thereto and also includes embodiments of which the following description provides examples.

DESCRIPTION OF THE INVENTION

This invention provides novel compounds of the formula (I) as defined above, which are potent inhibitors of purine nucleoside phosphorylase, nucleoside hydrolases and/or phosphoribosyltransferases.

The compounds of the invention are therefore expected to have clinical utility in treating conditions in which it is desirable to decrease the level of T lymphocyte activity, such as T-cell malignancies and autoimmune diseases, including arthritis and lupus. The invention also contemplates use of the compounds for immunosuppression for organ transplantation and for inflammatory disorders. The compounds of the invention are also expected to have utility in methods of treatment and/or prophylaxis of parasitic infections, particularly those caused by protozoan parasites, such as *Giardia, Trichomonas, Leishmania, Trypanosoma, Crithidia, Herpetomonas, Leptomonas, Histomonas, Eimeria, Isopora* and *Plasmodium*.

The compounds of formula (I) of the invention may be prepared by the methods described below:

Method A

This method may be used to prepare compounds of the formula (I) in which A is CR, where R is as defined above; ie compounds which are substituted at C-8 of the 9-deazapurine moiety.

The method comprises reacting a compound of formula (II)

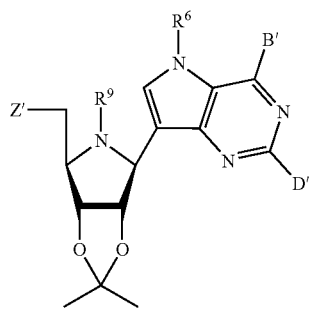

(II)

wherein $R^9$ is an alkoxycarbonyl or aralkyloxycarbonyl group, Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, and $R^6$ is an N-protecting group, B' and D' are independently selected from H, $OR^7$ and $N(R^8)_2$, and $R^7$ and $R^8$ are O- and N-protecting groups respectively;

(i) with a strong base capable of deprotonation at C-8 of the 9-deazapurine moiety; then
(ii) with an electrophile; and
(iii) O- and N-deprotecting the product by acid-, alkali- or fluoride ion-catalyzed hydrolysis or alcoholysis or catalytic hydrogenolysis as required for the O- and N-protecting groups in use.

Suitable strong bases are butyllithium and tert-butyllithium. Suitable electrophiles are N-fluorosulfomidobenzene, alkyl halides such as methyl iodide, aldehydes such as acetaldehyde, or formylating agents such as dime thylformamide.

A compound of formula (II) can be prepared as described in the applicants' PCT International patent application PCT/NZ00/00048 entitled "Processes for preparing inhibitors of nucleoside metabolism" and filed on Apr. 7, 2000, by N-protection of the product obtained by the coupling of a 1,N-dehydro-1,4-dideoxy-1,4-imino-D ribitol derivative with a protected 7-halogeno-deazapurine derivative (therein described as pyrrolopyrimidine derivatives).

More specifically, a compound of the formula (II) can be prepared by the following process:

(a) reacting a compound of the formula (IV)

(IV)

wherein Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, sequentially with a halogenating agent and a sterically hindered base to form an imine;

(b) condensing the imine thus prepared with an anion produced by abstraction of the bromine or iodine atom from a compound of formula (XIX): wherein $R^5$ is a bromine or iodine atom, $R^6$ is an N-protecting group, B' and

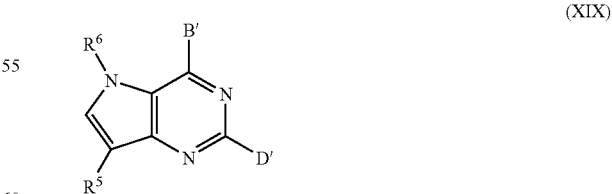

(XIX)

D' are independently selected from H, $OR^7$ and $N(R^8)_2$, and $R^7$ and $R^8$ are O- and N- protecting groups respectively, to produce a 1-C-(pyrrolo[3,2-d]pyrimidin-7-yl)-1,4-dideoxy-1,4-imino-2,3-O-isopropylidene-D-ribitol derivative of formula (II) as defined above, but in which $R^9$ is a hydrogen atom; and (c) converting the compound to a compound of formula (II) in which $R^9$ is alkoxycarbonyl or aralkoxycarbonyl.

The compounds of formula (II) where $R^9$ is a hydrogen atom can be converted into compounds of formula (II) where $R^9$ is an alkoxycarbonyl or aralkoxycarbonyl group by N-protecting with an appropriate compound containing the desired alkoxycarbonyl or aralkoxycarbonyl moiety. A suitable N-protecting group is the tert-butoxycarbonyl group, which can be introduced by the use of tert-butyl dicarbonate, for example in methylene chloride followed by chromatography.

The halogenating agent used in step (a) above may conveniently be N-chlorosuccinimide; and the hindered base used in step (a) may conveniently be lithium tetramethyl piperidide.

In step (b) above the bromide or iodine atom may conveniently be abstracted from the compound of formula (XIX) using butyllithium or magnesium.

The N-protecting group $R^6$ in the compound of formula (XIX) may conveniently be an alkoxymethyl group (such as benzyloxymethyl), a silyl group (such as tert-butyldimethylsilyl) or an arylmethyl group (such as benzyl). The O-protecting group $R^7$ may conveniently be an alkyl or arylmethyl group (such as methyl, tert-butyl or benzyl), and each N-protecting group $R^8$ may conveniently be independently an arylmethyl group (such as benzyl or 4-methoxybenzyl), or the two $R^8$ groups together may form the 2,4-hexadien-2,5-yl group.

The compounds of formula (XIX) defined above may be prepared by known methods. Compounds of the formula (IV) defined above may also be prepared by known methods, for example as described in WO 99/19338 and the references cited therein.

Method B

This method may be used to prepare compounds of the formula (I) in which W is H (ie 3'deoxy compounds of formula (I)).

This method comprises reacting a compound of formula (III)

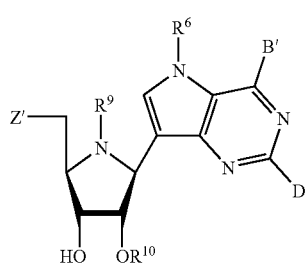

(III)

wherein $R^9$ is an alkoxycarbonyl or aralkyloxycarbonyl group, Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, and $R^6$ is an N-protecting group, B' and D' are independently selected from H, $OR^7$ and $N(R^8)_2$, $R^7$ and $R^8$ are O- and N-protecting groups, respectively, and $R^{10}$ is an O-protecting group;

(i) with a thiocarbonylating agent; then
(ii) with a radical reducing agent; and (iii) O- and N-deprotecting the product by acid-, alkali- or fluoride ion-catalyzed hydrolysis or alcoholysis or catalytic hydrogenolysis as required for the O- and N-protecting groups in use.

Together, steps (i) and (ii) are known as the Barton deoxygenation sequence. Suitable thiocarbonylating agents are thiocarbonyl diimidazole, phenoxythiocarbonyl chloride, or the combination of a base, carbon disulfide and methyl iodide. Suitable radical reducing agents are tributyltin hydride and lauroyl peroxide.

A compound of formula (III) can be prepared from a compound of formula (II) above by:

(i) removal of the 2,3-O-isopropylidene group by acid-catalyzed hydrolysis;
(ii) N-protection;
(iii) selective reprotection of the 5'-hydroxy-group if necessary; and
(iv) selective reprotection of the 2'-hydroxy-group.

Step (i) can conveniently be conducted by treatment with trifluoroacetic acid in an aqueous organic solvent under reflux. Certain 5'-O-protecting groups, such as a tert-butyldimethyl silyl group, may simultaneously be removed under these conditions, necessitating reprotection in step (iii). Reprotection can conveniently be achieved by treatment with a reagent capable of effecting selective protection of a primary hydroxy group in the presence of a secondary hydroxy group, such as trityl chloride and base.

A suitable N-protecting group is the tert-butoxycarbonyl group, which can be introduced by the use of tert-butyl dicarbonate in step (ii).

Selective protection of the 2'-hydroxy-group can be effected by activation of the 2',3'-diol as a stannylidene acetal, e.g. by reaction with dibutyltin oxide, and fluoride ion catalyzed reaction with a reagent capable of delivering an O-protecting group, such as 4-methoxybenzyl chloride and base.

Three preferred compounds of the present invention are:
(1S)-1-(9-deaza-8-fluorohypoxanthin-9-yl-1,4-dideoxy-1,4-imino-D-ribitol;
(1S)-1-(9-deaza-8-methylhypoxanthin-9-yl)-1,4-dideoxy-1,4-imino-D-ribitol; and
(1S)-1-(9-deazahypoxanthin-9-yl)-1,3,4-trideoxy-1,4-imino-D-ribitol.

These compounds may conveniently be prepared as their hydrochloride salts.

The compounds of the invention are useful both in free base form and in the form of salts. The term "pharmaceutically acceptable salts" is intended to apply to non-toxic salts derived from inorganic or organic acids, including for example salts derived from the following acids—hydrochloric, sulfuric, phosphonic, acetic, lactic, fumaric, succinic, tartaric, gluconic, citric, methanesulphonic and p-toluenesulphonic acids.

The dosage of the compound to be administered can vary widely according to the nature of the patient and the disorder being treated. However, typically the dosage for an adult human will be in the range of 0.1–1000 mg. The compounds can be administered in combination with one or more conventional pharmaceutical carriers or excipients and may be administered orally, by injection or topically.

The invention will be described in more detail with reference to the following non-limiting examples.

EXAMPLES

Example 1

Preparation of 5-O-tert-butyldimethylsilyl-1,N-dehydro-1,4-dideoxy-1,4-imino-2,3-O-isopropylidene-D-ribitol.

5-O-led-Butyldimethylsilyl-1,4-dideoxy-1,4-4-imino-2,3-O-isopropylidene-D-ribitol was treated with NCS and then lithium tetramethylpiperidide as described previously (Evans G. B.; Fumeaux, R. H.; Gainsford, G. J.; Schramm, V. L.; Tyler, P. C. *Tetrahedron* 2000, 56, 3053). The cold reaction mixture was partitioned between petroleum ether and water end processed normally. Chromatography of the residue (EtOAc/Petroleum ether/Triethylamine 100/200/1 v/v/v) afforded 5-O-tert-butyldimethylsilyl-1,N-dehydro-1,4-dideoxy-1,4-imino-2,3-O-isopropylidene-D-ribitol in ~80% yield which was used directly. cl Example 2

Preparation of 7-N-benzyloxymethyl-9-bromo-9-deaza-6-O-ethylhypoxanthine.

Sodium hydride (1.68 g, 80% dispersion, 47 mmol) was added to a stirred suspension of 6-chloro-9-deazapurine (K. Imai, *Chem. Pharm. Bell.* 1964, 12, 1030) (5.19 g, 33.8 mmol) In THF (80 mL) and the resulting mixture was stirred in an ice bath while benzyl chloromethyl ether (6 mL, 43 mmol) was added slowly. The mixture was then stirred at room temperature for 1 h. Methanol (20 mL) and sodium hydride (1.6 g. 60%, 40 mmol) were added carefufly and then after 1 h NBS was added portion-wise until t.l.c. analysis indicated the initial material was replaced by a less polar product. The solution was washed with water (×2), and processed normally. Chromatography afforded 7-N-benzyloxymethyl-9-bromo-9-deaza-6-O-methylhypoxanthine (6.83 g, 19.6 mmol) as a solid. Recrystallized from ethanol it had m.p. 98–99° C.; $^1$H NMR δ 8.60 (s; 1H), 7.44 (s, 1H), 7.35–7.21 (m, 5H), 5.71 (s, 2H), 4.48 (s, 2H), 4.11 (s, 3H); $^{13}$C NMR δ 156.8 (C), 151.4 (CH), 148.8, 136.9 (C), 131.9, 128.9, 128.5, 128.0 (CH), 116.0, 92.8 (C), 77.6, 70.8 (CH$_2$), 54.2 (CH$_3$). Anal. calc. for C$_{15}$H$_{14}$BrN$_3$O$_2$: C, 51.74; H, 4.05; Br, 22.95; N, 12.07. Found: C, 51.97; H, 3.91; Br, 23.19; N, 12.28.

Example 3

Preparation of 7-N-benzyloxymethyl-9-bromo-6-O-tert-butyl-9-deazahypoxanthine.

Sodium hydride (60% dispersion, ~1.5 g) was added slowly to a stirred suspension of 6-chloro-9-deazapurine (5.0 g) and chloromethyl benzyl ether (6 mL) in dry THF (100 mL) in an ice bath until effervescence had ceased. Then tert-butyl alcohol (20 mL), DMF (20 mL) and more sodium hydride (60%, 1.5 g) were added, the cooling bath was removed and the mixture was stirred at rt for 24 h. Chloroform (200 mL) was added and the mixture was washed with water (×2) and processed normally. A solution of the crude residue in chloroform (50 mL). was stirred in an ice bath while NBS (~5 g) was added portion-wise until TLC indicated the reaction was complete. Chromatography then afforded 7-N-benzyloxymethyl-9-bromo-6-O-tert-butyl-9-deazahypoxanthine as a pale yellow solid (5.8 g). $^1$H NMR (CDCl3) δ 8.55 (1H, s), 7.41 (1H, s), 7.34–7.20 (5H, m), 5.73 (2H, s), 4.48 (2H, s), 1.69 (9H, s); $^{13}$C NMR (CDCl3) δ 156.3 (C), 151.1 (CH), 148.7, 137.1 (C), 131.4, 128.9, 128.4, 127.8 (CH), 117.0, 92.6, 84.0 (C), 77.6, 70.5 (CH$_2$), 29.0 (CH$_3$).

Example 4

Preparation of 1-(S)-(7-N-benzyloxymethyl-6-O-tert-butyl-9-deazahypoxanthin-9-yl)-N-tert-butoxycarbonyl-5-O-tert-butyldimethylailyl-1,4-dideoxy-1,4-imino-2,3-O-isopropylidene-D-ribitol.

A solution of the product from example 3 (2.7 g) in anlsole (20 ml) and ether (40 mL) was cooled to −60° C. and butyl lithium (2.9 ml, 2.4 M in hexanes) was added. Then a solution of the product from example 1 (1.6 g) in ether (5 ml) was added. The solution was allowed to warm slowly to 10° C. and then washed with water, dried and concentrated to dryness. Chromatography afforded the product mixed with the debrominated deazahypoxanthine derivative. The mixture was dissolved In dichloromethane (20 ml) and di tert-butyl-dicarbonate (1.05 g) was added. After 1 h the solution was concentrated and chromatography afforded 1-(S)-(7-benzyloxymethyl-6-O-tert-butyl-9-deazahypoxanthin-9-yl)-N-tert-butoxycarbonyl-5-O-tert-butyldimethylsilyl-1,4-dideoxy-1,4-imino-2,3-O-isopropylidene-D-ribitol (2.17 g).

Example 5

Preparation of 1-(S)-(7-N-benzyloxymethyl-9-deaza-6-O-methylhypoxanthin-9-yl)-N-tert-butoxycarbonyl-5-O-tert-butyldimethylsilyl-1,4-dideoxy-1,4-imino-2,3-O-isopropylidene-D-ribitol.

A solution of the product from example 2 (16.0 g, 46 mmol) in anisole (120 ml) and ether (200 mL) was treated with butyl lithium at −35° C. and then the product from example 1 as described above In example 4. The crude product in methylene chloride (100 ml) was treated with di-tert-butyl dicarbonate (8.0 g. 36 mmol) and the solution was stirred for 1 h, then concentrated to dryness. Chromatography of the residue afforded 1-(S)-(7-N-benzyloxymethyl-9-deaza-6-O-methylhypoxanthin-9-yl)-N-tert-butoxycarbonyl-5-O-tert-butyldimethylsilyl-1,4-imino-2,3-O-isopropylidene-D-ribitol (18.8 g, 28.7 mmol) as a syrup. $^1$H NMR (C$_6$D$_6$ at 70° C.) δ 8.67 (1H, s), 7.48 (1H, br s), 7.09 (5H, m), 5.78 (1H, br s), 5.67 (1H, s), 5.44 (1H, br s), 5.25 (2H, s), 4.54 (1H, br s), 4.23 (2H, s), 4.09 (1H, t, J=9.7 Hz), 3.97 (1H, br s), 3.77 (3H, s), 1.57 (3H, s), 1.42 (9H, s), 1.33 (3H, s), 0.97 (9H, s), 0.11 (6H, s); $^{13}$C NMR (C$_6$D$_6$ at 70° C.) δ 156.7, 154.8 (C), 150.4 (CH), 149.4, 137.9, 133.8, 116.4, 111.9 (C), 84.6, 84.0 (CH), 79.6 (C), 77.3, 70.4 (CH$_2$), 67.7 (CH), 63.4 (CH$_2$), 61.9 (CH), 53.0 (CH$_3$), 28.7, 27.9, 26.3, 25.8 (CH$_3$), 18.6 (C), −4.9, −5.0 (CH$_3$). Some aromatic signals were obscured by the solvent. HRMS (MH$^+$) calc. for C$_{34}$H$_{51}$N$_4$O$_7$Si: 655.3527. Found: 655.3553.

Example 6

Preparation of (1S)-1-(9-deaza-8-fluorohypoxanthin-9-yl)-1,4-dideoxy-1,4-imino-D-ribitol hydrochloride.

A solution of the product from example 4 (1.25 g) in THF (30 mL) was cooled to −70° C. and butyl lithium (1.5 mL, 2.4 M in hexanes) was added slowly. After 10 mins N-fluorobenzenesulfonimide (1.42 g) was added to the red/brown solution. After 20 mins the solution was partitioned between water and chloroform. The organic phase was processed normally and chromatography afforded 1-(S)-(7-N-benzyloxymethyl-6-O-tert-butyl-9-deaza-8-fluorohypoxanthin-9-yl)-N-tert-butoxycarbonyl-5-O-tert-butyldimethylsilyl-1,4- dideoxy-1,4-imino-2,3-O-isopropylidene-D-ribitol (0.67 g). A solution of 0.2 g of this material in THF (5 mL) and methanol (5 ml) was stirred with tetrabutylammonium fluoride (5 mL, 1 M in THF) for 18 h. The solution was concentrated end a solution of the residue In toluene (15 ml) was washed with water (×2), dried and concentrated to dryness. The residue in ethanol (10 ml) was stirred under hydrogen in the presence of 10% Pd/C (0.2 g) for 18 h. The solids and solvent were removed and chromatography afforded two products, one with and one without the 6-O-tert-butyl residue on the hypoxanthine moiety. These were combined in methanol (4 mL) and 2M aq HCl (4 mL) was added. After 2 h the solution was concentrated to dryness and the residue was recrystallised from aq acetone to give (1S)-1-(9-deaza-8-fluorohypoxanthin-9-yl)-1,4-dideoxy-1,4-imino-D-ribitol hydrochloride (0.043 g). $^1$H NMR (D$_2$O) δ 8.04 (1H, s), 4.97–4.88 (2H, m), 4.48 (1H, t, J=4.1 Hz), 3.93 (2H, m), 3.89 (1H, dd, J=4.6, 9.0 Hz). Anal. calc. for C$_{11}$H$_{14}$ClFN$_4$O$_4$: requires C, 41.20; H, 4.40; Cl, 11.05; N, 17.47. Found: C, 41.01; H, 4.37; Cl, 11.11; N, 17.17.

Example 7

Preparation of (1S)-1-(9-deaza-8-methylhypoxanthin-9-yl)-1,4-dideoxy-1,4-imino-D-ribitol Hydrochloride.

A solution of the product from example 5 (0.29 g) in THF (7 mL) was cooled to −70° C. and butyl lithium (0.4 mL, 2.4 M in hexanes) was added slowly. After 10 mins methyl iodide (0.25 mL) was added and 10 mins later the solution was partitioned between chloroform and water and the organic layer was processed normally followed by chromatography affording the 8-C-methyl product (0.164 g). This material in ethanol (5 mL) was stirred under hydrogen with 10% Pd/C (0.1 g) for 3 days. Removal of the solids and solvent and chromatography afforded 1-(S)-(9-deaza-6-O-methylhypoxanthin-9-yl)-N-tert-butoxycarbonyl-1,4-dideoxy-1,4-imino-2,3-O-isopropylidene-D-ribitol (0.089 g). A solution of this material in methanol (3 mL) and conc aq HCl (3 mL) was heated under reflux for 2 h and then concentrated to dryness to give (1S)-1-(9-deaza-8-methyl-hypoxanthin-9-yl)-1,4-dideoxy-1,4-imino-D-ribitol hydrochloride (0.061 g) as a white solid. $^1$H NMR (D$_2$O) δ 8.46 (1H, s), 4.96 (1H, dd, J=9.4, 4.6 Hz), 4.89 (1H, d, J=9.5 Hz), 4.51 (1H, m), 4.07 (2H, m), 3.96 (1H, m,), 2.54 (3H, s). Anal. calc. for C$_{12}$H$_{17}$ClN$_4$O$_4$: C, 45.50; H, 5.41; Cl, 11.19; N, 17.69. Found: C, 45.38; H, 5.41; Cl, 11.50; N, 17.80.

Example 8

Preparation of 1-(S)-(7-N-benzyloxymethyl-9-deaza-6-O-methylhypoxanthin-9-yl)-1,4-dideoxy-1,4-imino-2,3-O-isopropylidene-D-ribitol.

A solution of the product from example 2 (4.4 g, 12.6 mmol) in anisole (60 mL) and ether (100 mL) was treated with butyl lithium and then the product from example 1 (2.4 g, 8.4 mmol) as described above in example 4, except that it was not treated with di tert-butyl-dicarbonate. Tetrabutylammonium fluoride (15 mL, 1 M in THF) was added to a solution of the crude product in THF (20 mL) and after 1 h toluene (100 mL) was added and the solution was washed with water (×2) and then processed normally. Chromatography afforded syrupy 1-(S)-(7-N-benzyloxymethyl-9-deaza-6-O-methylhypoxanthin-9-yl)-1,4-dideoxy-1,4-imino-2,3-O-isopropylidene-D-ribitol (2.27 g, 5.16 mmol). $^1$H NMR (CDCl$_3$) δ 8.51 (s, 1H), 7.38 (s, 1H), 7.35–7.22 (m, 5H), 5.73 (d, J=10.6 Hz, 1H), 5.65 (d, J=10.6 Hz, 1H), 4.89 (t, J=5.7 Hz, 1H), 4.77 (dd, J=6.0, 2.1 Hz, 1H), 4.50 (d, J=5.5 Hz, 1H), 4.48 (s, 2H), 4.09 (s, 3H), 3.74 (s, 1H), 3.73 (s, 1H), 3.64 (dd, J=5.3, 2.9 Hz, 1H), 1.61 (s, 3H), 1.36 (s, 3H); $^{13}$C NMR δ 156.8 (C), 150.1 (CH), 149.2, 137.3 (C), 130.9, 128.8, 128.4, 128.0 (CH), 118.3, 117.1, 113.1 (C), 86.1, 83.9 (CH), 77.3, 70.6 (CH$_2$), 64.7, 64.6 (CH and CH$_2$), 62.5 (CH), 54.0, 28.2, 25.8 (CH$_3$). HRMS (MH$^+$) calc. for C$_{23}$H$_{29}$N$_4$O$_5$: 441.2138. Found: 441.2115.

Example 9

Preparation of (1S)-1-(9-deazahypoxanthin-9-yl)-1,3,4-trideoxy-1,4-imino-D-ribitol hydrochloride.

A solution of the product from example 8 (2.27 g) in THF (30 mL), water (12.5 mL) and trifluoroacetic acid (2.5 mL) was heated under reflux for 1.5 h and then concentrated to dryness. The residue in methanol. (10 mL) was treated with triethylamine (1.5 mL) and di tert-butyl-dicarbonate (1.67 g). After 1 h the solution was concentrated to dryness and chromatography afforded 1-(S)-(7-N-benzyloxymethyl-9-deaza-6-O-methylhypoxanthin-9-yl)-N-tert-butoxycarbonyl-1,4-dideoxy-1,4-imino-D-ribitol (2.28 g). To a solution of 1.74 g of this material in dichloromethane (20 mL) was added diisopropylethylamine (2.4 mL), trityl chloride (1.17 g) and 4-dimethylaminopyridine (0.13 g). After 16 h at room temperature more trityl chloride (1.0 g) was added and after a further 8 h the solution was processed normally followed by chromatography to give 1-(S)-(7-N-benzyloxymethyl-9-deaza-6-O-methylhypoxanthin-9-yl)-N-tert-butoxycarbonyl-1,4-dideoxy-1,4-imino-5-O-triphenylmethyl-D-ribitol (2.27 g). Dibutyltin oxide (0.17 g) was added to a solution of 0.5 g of this material in benzene (15 mL) and the mixture was heated under reflux under a Dean Stark apparatus for 1 h. Then tetrabutylammonium bromide (0.217 g) and 4-methoxybenzyl chloride (0.183 mL) were added and the solution was heated under reflux for 16 h. After concentrating to dryness chromatography of the residue afforded 1-(S)-(7-N-benzyloxymethyl-9-deaza-6-O-methylhypoxanthin-9-yl)-N-tert-butoxycarbonyl-1,4-dideoxy-1,4-imino-2-0-(4-methoxybenzyl)-5-O-triphenylmethyl-D-ribitol (0.377 g) as the major product. A solution of this material in toluene (5 mL) containing thiocarbonyl diimidazole (0.148 g) was heated under reflux for 1 h. Tributyltin hydride (1 mL) was added and the solution was refluxed for a further 0.5 h. After concentrating to dryness the residue in acetonitrile was washed (×2) with petroleum ether and concentrated to dryness. Chromatography of the residue then afforded 1-(S)-(7-N-benzyloxymethyl-9-deaza-6-O-methylhypoxanthin-9-yl)-N-tert-butoxycarbonyl-1,4-imino-2-0-(4-methoxybenzyl)-1,3,4-trideoxy-5-O-triphenylmethyl-D-ribitol (0.204 g). This material was suspended in conc. aq. HCl (5 mL) and the mixture was heated under reflux for 1 h, cooled and concentrated to dryness. Water (10 mL) was added to the residue and the mixture was extracted (×2) with chloroform. The aqueous phase was concentrated to dryness and chromatography of the residue afforded a white solid which was treated with aq. HCl and lyophilised to give (1S)-1-(9deazahypoxanthin-9-yl)-1,3,4-trideoxy-1,4-imino-D-ribitol hydrochloride (0.06 g) as a white solid. $^1$H NMR (D$_2$O) δ 7.95 (1H, s), 7.68 (1H, s), 4.95–4.84 (2H, m), 4.21 (1H, m), 3.97 (1H, dd, J=3.8, 12.6 Hz), 3.83 (1H, dd, J=6.7, 12.6 Hz), 2.46 (1H, m), 2.30 (1H, m); $^{13}$C NMR δ 157.5, 146.0 (C), 145.3, 131.4 (CH), 120.4, 110.8 (C), 76.2, 63.8 (CH), 63.1 (CH$_2$), 62.7 (CH), 36.6 (CH$_2$). HRMS (MH) calc. for C$_{11}$H$_{15}$N$_4$O$_3$: 251.1144. Found: 251.1133.

Determination of Inhibition Constants for Bovine Purine Nucleoside Phosphorylase The inhibition constants for the compounds (1S)-1-(9-deaza-8-fluorohypoxanthin-9-yl)-1,4-dideoxy-1,4-imino-D-ribitol hydrochloride, (1S)-1-(9-deaza-8-methylhypoxanthin-9-yl)-1,4-dideoxy-1,4-imino-D-ribitol hydrochloride and (1S)-1-(9-deazahypoxanthin-9-yl)-1,3,4-trideoxyl-1,4-dideoxy-1,4-imino-D-ribitol hydrochloride were determined as described in Miles et al (*Biochemistry* 37, 8615 (1998)) using bovine purine nucleoside phosphorylase (Sigma). $K_i^*$ is the equilibrium dissociation constant for the PNP•inhibitor complex following slow-onset inhibition. It governs the biological properties of PNP inhibition. Not all inhibitors exhibit slow-onset binding, and others have not been experimentally examined for slow-onset inhibition. Where known, slow-onset properties are indicated. $K_i$ and $K_i^*$ values determined are shown below.

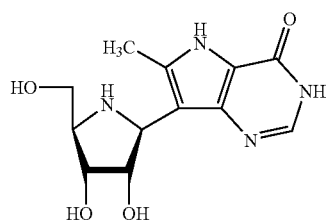

$K_i$ = 90 pM
2/3 partial inhibition only

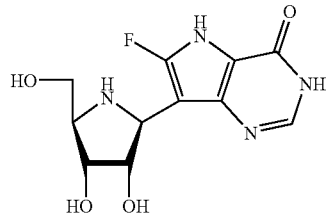

$K_i^*$ = 140 pM

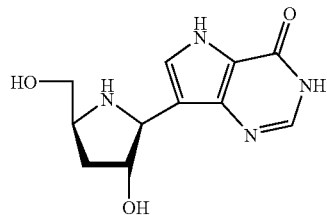

$K_i$ = 1 nM
no slow onset

Although the invention has been described with reference to specific embodiments, those persons skilled in the art will appreciate that variations and modifications can be made without departing from the scope of the invention.

INDUSTRIAL APPLICABILITY

The compounds of the present invention are potent inhibitors of purine nucleoside phosphorylase, nucleoside hydrolases and/or phosphoribosyl transferases. The compounds are therefore expected to have utility in treating conditions such as T-cell malignancies and autoimmune diseases. The compounds may also be useful in immunosuppression for organ transplant and inflammatory diseases.

In addition, the compounds of the invention are expected to be useful in the treatment and/or prophylaxis of parasitic infections, particularly those caused by protozoan parasites.

What is claimed is:
1. A compound of the formula:

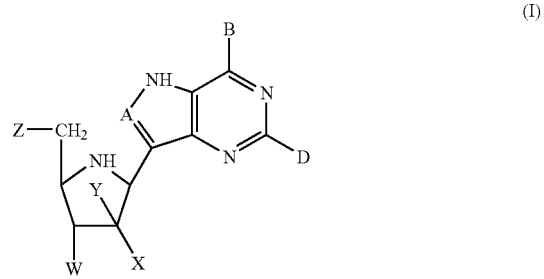

wherein:
A is CH or CR, where R is selected from halogen, optionally substituted alkyl, aralkyl and aryl, OH, $NH_2$, $NHR^1$, $NR^1R^2$ and $SR^3$, where $R^1$, $R^2$ and $R^3$ are each optionally substituted alkyl, aralkyl or aryl groups;
B is OH;
D is selected from OH, $NH_2$, $NHR^5$, H, halogen and $SCH_3$, where $R^5$ is an optionally substituted alkyl, aralkyl or aryl group;
X and Y are independently selected from H, OH and halogen, with the proviso that when one of X and Y is hydroxy or halogen, the other is hydrogen;
Z is OH, or, when X is hydroxy, Z is selected from hydrogen, halogen, hydroxy, SQ and OQ, where Q is an optionally substituted alkyl, aralkyl or aryl group; and
W is OH or H, with the proviso that when W is OH, then A is CR where R is as defined above;
or a tautomer thereof; or a pharmaceutically acceptable salt thereof.

2. A compound as claimed in claim 1, wherein D is $NHR^5$, and $R^5$ is $C_1$–$C_4$ alkyl.

3. A compound as claimed in claim 1 wherein when one or more halogens are present, they are chosen from chlorine or fluorine.

4. A compound as claimed in claim 1 wherein when Z is SQ or OQ, Q is $C_1$–$C_5$ alkyl or phenyl.

5. A compound as claimed in claim 1 wherein either D is H.

6. A compound as claimed in claim 1 wherein D is H, OH or $NH_2$, X is OH or H and Y is H.

7. A compound as claimed in claim 1 wherein Z is OH, H or methylthio.

8. A compound as claimed in claim 1 wherein W is OH, Y is H, X is OH, and A is CR where R is methyl or halogen.

9. A compound as claimed in claim 1 wherein W is H, Y is H, X is OH and A is CH.

10. A compound as claimed in claim 1 selected from
(1S)-1-(9-deaza-8-fluorohypoxanthin-9-yl)-1,4-dideoxy-1,4-imino-D-ribitol;
(1S)-1-(9-deaza-8-methylhypoxanthin-9-yl)-1,4-dideoxy-1,4-imino-D-ribitol; or
(1S)-1-(9-deazahypoxanthin-9-yl)-1,3,4trideoxy-1,4-imino-D-ribitol;
or a tautomer thereof; or a pharmaceutically acceptable salt thereof.

11. A composition comprising a compound of the formula (I) as claimed in claim 1, and a carrier or diluent.

12. A method for preparing a compound of the formula (I) as defined in claim 1, wherein A is CR and R is as defined in claim 1, the method comprising reacting a compound of formula (II)

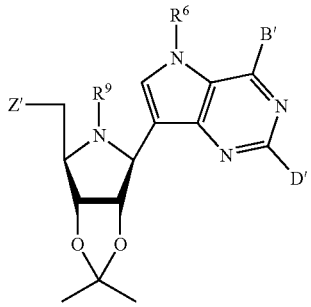

wherein $R^9$ is an alkoxycarbonyl or aralkyloxycarbonyl group, Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, and $R^6$ is an N-protecting group, B' and D' are independently selected from H, $OR^7$ and $N(R^8)_2$, and $R^7$ and $R^8$ are O- and N-protecting groups respectively;
  (i) with a strong base capable of deprotonation at C-8 of the 9-deazapurine moiety; then
  (ii) with an electrophile selected from the group consisting of an alkyl halide, an aldehyde, a formylating agent and N-fluorosulfomidobenzene; and
  (iii) O- and N-deprotecting the product by acid-, alkali- or fluoride ion-catalyzed hydrolysis or alcoholysis or catalytic hydrogenolysis as required for the O- and N-protecting groups in use.

13. A method as claimed in claim 12 wherein the strong base comprises butyllithium.

14. A method for preparing a compound of the formula (I) as defined in claim 1, wherein W is H, the method comprising reacting a compound of formula (III)

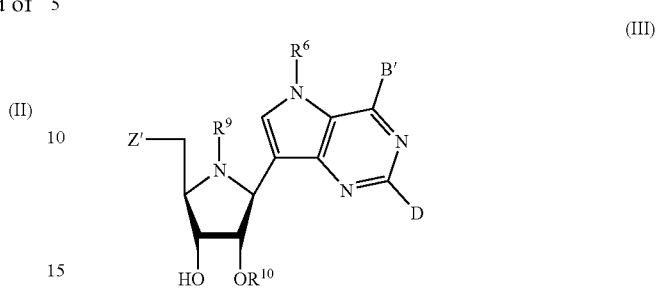

wherein $R^9$ is an alkoxycarbonyl or aralkyloxycarbonyl group, Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, and $R^6$ is an N-protecting group, B' and D' are independently selected from H, $OR^7$ and $N(R^8)_2$, $R^7$ and $R^8$ are O- and N-protecting groups, respectively, and $R^{10}$ is an O-protecting group;
  (i) with a thiocarbonylating agent; then
  (ii) with a radical reducing agent; and
  (iii) O- and N-deprotecting the product by acid-, alkali- or fluoride ion-catalyzed hydrolysis or alcoholysis or catalytic hydrogenolysis as required for the O- and N-protecting groups in use.

15. A method as claimed in claim 14 wherein the thiocarbonylating agent is thiocarbonyl diimidazole.

16. A method as claimed in claim 14 wherein the radical reducing agent comprises tributyltin hydride.

17. The method of claim 12, wherein the electrophile is N-fluorosulfomidobenzene.

18. The method of claim 12, wherein the electrophile is methyl iodide, acetaldehyde or dimethylformamide.

* * * * *

UNITED STATES PATENT AND TRADEMARK OFFICE
CERTIFICATE OF CORRECTION

PATENT NO.        : 7,109,331 B2                                                      Page 1 of 1
APPLICATION NO.   : 10/363424
DATED             : September 19, 2006
INVENTOR(S)       : Richard Hubert Fumeaux, Peter Charles Tyler and Vern L. Schramm It is certified that error appears in the above-identified patent and that said Letters Patent is hereby corrected as shown below:

Column 5, Lines 46-55, and Column 14, Lines 6-16, replace the structure with the following structure:

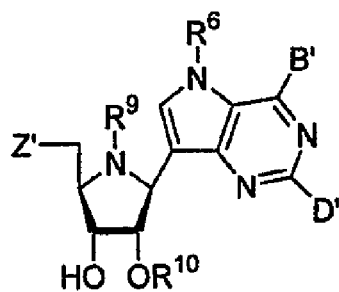

Signed and Sealed this

Twenty-second Day of May, 2007

JON W. DUDAS
*Director of the United States Patent and Trademark Office*